(12) United States Patent
Schmid

(10) Patent No.: US 7,311,195 B2
(45) Date of Patent: Dec. 25, 2007

(54) MIXING CAPSULE AND METHOD FOR ACTIVATING THE SAME

(75) Inventor: Daniel Schmid, Gossau (CH)

(73) Assignee: Alfred Schmid AG Gossau, Gossau (CH)

( * ) Notice: Subject to any disclaimer, the term of this patent is extended or adjusted under 35 U.S.C. 154(b) by 105 days.

(21) Appl. No.: 10/491,286

(22) PCT Filed: Oct. 1, 2002

(86) PCT No.: PCT/CH02/00546

§ 371 (c)(1),
(2), (4) Date: Aug. 10, 2004

(87) PCT Pub. No.: WO03/028871

PCT Pub. Date: Apr. 10, 2003

(65) Prior Publication Data

US 2004/0251147 A1 Dec. 16, 2004

(30) Foreign Application Priority Data

Oct. 1, 2002 (CH) .................................... 1796/01

(51) Int. Cl.
*B65D 25/08* (2006.01)
*B67D 5/56* (2006.01)
(52) U.S. Cl. .................. 206/219; 222/129; 215/DIG. 8
(58) Field of Classification Search ............... 222/83, 222/129, 142.5, 145.1, 145.5, 145.8, 433, 222/490, 327, 326, 386, 319, 80, 82; 206/219, 206/220, 63.5; 215/DIG. 8; 433/90
See application file for complete search history.

(56) References Cited

U.S. PATENT DOCUMENTS

| 2,629,889 | A | * | 2/1953 | Aline .......................... 401/174 |
| 3,134,517 | A | * | 5/1964 | Seybold ....................... 222/319 |
| 3,144,966 | A | * | 8/1964 | Cook ........................... 222/136 |
| 3,543,967 | A | * | 12/1970 | O'Connor .................... 222/136 |
| 3,595,439 | A | * | 7/1971 | Newby et al. ................. 222/80 |
| 3,655,037 | A | * | 4/1972 | Lussier ....................... 206/222 |
| 4,470,505 | A | * | 9/1984 | Korwin et al. .............. 206/219 |
| 4,648,532 | A | * | 3/1987 | Green .......................... 222/82 |
| 4,858,759 | A | * | 8/1989 | Mauthe et al. .............. 206/221 |
| 4,941,751 | A | * | 7/1990 | Muhlbauer ............... 366/182.1 |

(Continued)

FOREIGN PATENT DOCUMENTS

DE 42 32 062 A 4/1993

(Continued)

*Primary Examiner*—Kevin Shaver
*Assistant Examiner*—Stephanie E. Tyler
(74) *Attorney, Agent, or Firm*—Nixon & Vanderhye P.C.

(57) ABSTRACT

A mixing capsule for a two-component mixture comprises a preferably cylindrical container part. An axially displaceable piston is guided within the container part. An opening is provided on the front face of the piston and leads into a liquid receptacle with a burstable wall or membrane. The membrane closes the opening in the non-activated condition of the capsule. The hollow between the front faces of the container part and the piston constitutes a mixing chamber. The activation part can be displaced by means of activation pin that closes the discharge nozzle in the non-activated condition. In the activated condition of the capsule the activation part is to all intents and purposes completely accommodated within the liquid receptacle.

23 Claims, 3 Drawing Sheets

U.S. PATENT DOCUMENTS

| | | | |
|---|---|---|---|
| 5,127,548 A * | 7/1992 | Brunet et al. | 222/80 |
| 5,172,807 A * | 12/1992 | Dragan et al. | 206/219 |
| 5,392,904 A * | 2/1995 | Frick et al. | 206/219 |
| 6,715,645 B2 * | 4/2004 | Peuker et al. | 222/129 |
| 6,739,478 B2 * | 5/2004 | Bach et al. | 222/1 |

FOREIGN PATENT DOCUMENTS

| | | |
|---|---|---|
| DE | 43 15 920 C | 12/1994 |
| EP | 0 245 788 A | 11/1987 |
| GB | 1 326 289 A | 8/1973 |
| WO | 00/45732 A | 8/2000 |

* cited by examiner

MIXING CAPSULE AND METHOD FOR ACTIVATING THE SAME

This application is the U.S. national phase of international application PCT/CH002/00546 filed in Deutsch on 01 Oct. 2002, which designated the U.S. PCT/CH002/00546 claims priority to CH Application No. 1796/01 filed 01 Oct. 2001. The entire contents of these applications are incorporated herein by reference.

FIELD OF INVENTION

The invention relates to a mixing capsule a two-component mixture and a method of activating a mixing capsule containing at least two components of a multi-component mixture.

EPA-A-0 245 788 discloses a mixing capsule for a two-component mixture with a cylindrical housing with an integrated discharge nozzle and a piston capable of moving axially within the cylindrical housing. The circumference of the piston is provided with a thread that can engage with a corresponding internal thread of the cylindrical housing. The front face of the piston has a central opening through which a liquid can flow into the interior of the piston. A liquid cushion arranged on the front face of the piston serves as liquid reservoir. The liquid cushion is provided with a membrane adjacent to the front face of the piston that will burst (explode) in the event of an overpressure in the region of the opening. The rear face of the piston is closed with a plug and the space within the piston serves to contain the pulverous component of the two-component mixture. When the components are to be mixed, the piston is screwed into the housing until the membrane bursts and the liquid pours into the interior of the piston. The bursting of the membrane causes it to fray and parts of the membrane may find their way into the mixing chamber.

A mixing capsule similar to EP-A-0-245788 is disclosed by U.S. Pat. No. 5,026,283. In this case, once again, the membrane separating the liquid package from the mixing chamber is made to burst by the application of an overpressure. Consequently, loose pieces of the membrane can reach the mixing chamber even with this capsule. If the mixture is to be discharged, the front membrane of the liquid package must first be punctured from the rear with the help of a pin arranged on another piston.

A characteristic feature of the capsules described above is that parts of the membrane can find their way into the mixing chamber and therefore into the mixture when the capsule is activated. Another drawback is that the activation of the capsule causes an overpressure in the mixing chamber. The overpressure is due to the fact that an additional volume, namely the liquid, is pressed into the mixing chamber. But an overpressure during the mixing has the effect that gas is pressed into the mixture and that undesired gas bubbles can therefore form when it is discharged.

BRIEF DESCRIPTION OF THE INVENTION

The present invention sets out to make available a mixing capsule in which no membrane fragments can reach the mixing chamber when it is activated. A further aim is to create a capsule that can be activated with small energy consumption. Another object is to suggest a capsule in which the danger of bubble formation is small. Furthermore, it is proposed to make available a capsule that can be economically produced and charged.

A capsule in accordance with the invention is characterized in that a movable activation part is provided in the hollow between the faces of the container part and the piston that defines the mixing chamber. This capsule has the advantage that the activation part punctures the membrane in the direction of the liquid and that no membrane parts will therefore find their way into the mixing chamber. Furthermore, only a small force is needed to puncture the membrane. Accordingly, no threads have to be provided on the container part and the piston. A further advantage is that the volume of the mixing chamber remains constant during the activation process, i.e. when the components stored in the mixing chamber and the liquid receptacle are brought together, and that no overpressure is therefore produced. Over and above the activation function, the activation part in accordance with the invention also has the function of a displacement organ that removes the liquid component from the liquid receptacle. Advantageously, the activation part substantially fits into the opening on the front face of the piston, i.e. the respective outer and inner diameters of the part and the opening are substantially identical. This has the advantage that the membrane is held by the activation part after the latter has been pushed inwards and that no membrane fragments can therefore reach the mixing chamber. Preferably, the activation part can be displaced by means of an activation pin that closes the discharge nozzle in the non-activated condition.

Advantageously, the form of the activation part will be the complement of the liquid receptacle. Consequently, the activation part can expel the liquid within the receptacle into the mixing chamber. A further advantage is that the membrane is fixed in the liquid receptacle by the activation or displacement part. Advantageously, the activation part will be situated in the liquid receptacle after activation in such a manner as to be substantially flush with the front face of the piston. This has the advantage that the piston can practically completely discharge the finished mixture from the capsule.

Although in general principle the liquid receptacle may be a package made from a foil, the liquid is preferably contained a liquid receptacle formed on the piston. According to a particularly preferred embodiment, the piston is itself designed as the liquid receptacle or integrally attached thereto. This is a simple construction and can be produced at a correspondingly low cost. Advantageously, a membrane covering the opening is or can be applied to the front face of the piston. Since the wall of the piston has a predetermined wall thickness, the foil can be readily welded onto the front face. When this is done, there is practically no danger that a part of the liquid could evaporate. Advantageously, at least a gasket will be formed on the front of the piston jacket. This assures the sealing of the mixing chamber defined by the front faces container part and the piston.

Advantageously, the front part of the activation part is designed as a tip. This makes it possible for the foil closing the liquid receptacle to be punctured with a small energy expenditure. According to a preferred embodiment, an overflow channel or gutter running in the axial direction is provided on the jacket of the activation part. The overflow channel may prevent a pressure build-up in the liquid receptacle, because the liquid can easily flow out. Furthermore, the overflow channel can be dimensioned in such a manner as to enable even viscous or sticky media to leave the liquid receptacle.

In basic principle the activation pin may be formed directly on the activation part. In that case the activation part together with the activation pin can be inserted into the container part from behind. A preset breaking at the bottom of the activation part makes it possible for the activation pin to be separated and withdrawn after the mixing process, for example by turning it. According to a preferred embodiment, however, activation part and activation pin are designed as separate parts. In this embodiment it is advantageous to provide a recess on the bottom of the activation part as guide for the activation pin. The activation part can be fitted onto the activation that has previously been inserted into the discharge nozzle. Advantageously, the activation part is a filling body with a flat bottom. The filling body may be made of plastic material and have a form that is complementary to the liquid receptacle. Advantageously, the filling body will fit into the liquid receptacle more or less flush with the front face of the piston.

According to a particularly preferred embodiment, the length of the activation pin is such that the piston of the filled mixing capsule may be pulled back over a certain distance from a filling position to a mixing position. The volume enlargement produces an underpressure in the mixing chamber. This has the advantage that the mixture is degassed during the mixing. Consequently, no bubbles will form when the mixture is discharged.

Another object of the present invention is a method of mixing a mixing capsule containing at least two components of a multi-component mixture, characterized in that the membrane is destroyed by pushing a mobile activation part provided inside the mixing chamber into the liquid receptacle. Since the membrane is pushed into the liquid receptacle, there is no danger that parts of the membrane will find their way into the mixing chamber. Advantageously, the activation part presses the liquid from the liquid receptacle into the mixing chamber. Preferably, the mixing chamber is enlarged before the mixing, so that the mixing process takes place at a reduced pressure. This has the advantage that a degassing of the mixture may take place during the mixing.

BRIEF DESCRIPTION OF THE DRAWING

By way of example, the invention will now be described with reference to the figures, of which.

DETAILED DESCRIPTION OF THE DRAWINGS

Figure 1:
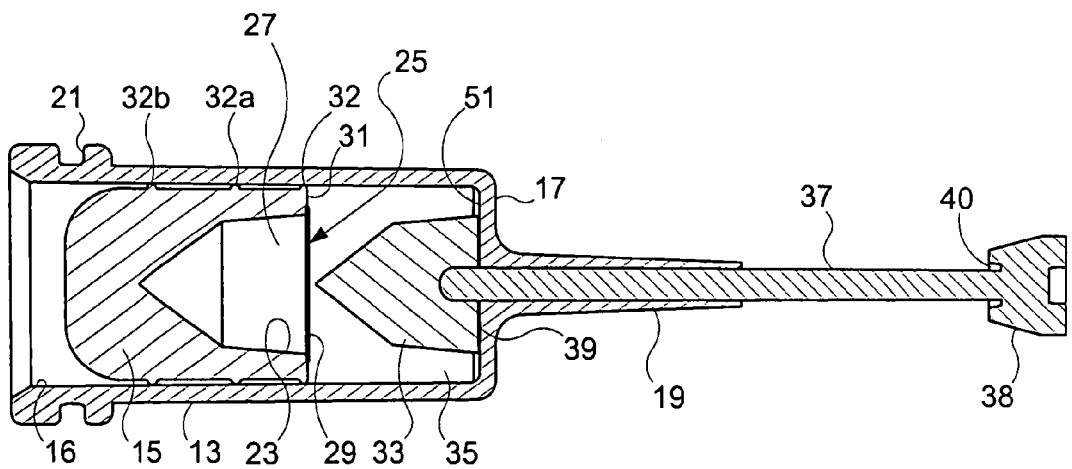
FIG. 1 shows a longitudinal section through a mixing capsule in accordance with the invention in the filled position (initial condition)
Figure 2:
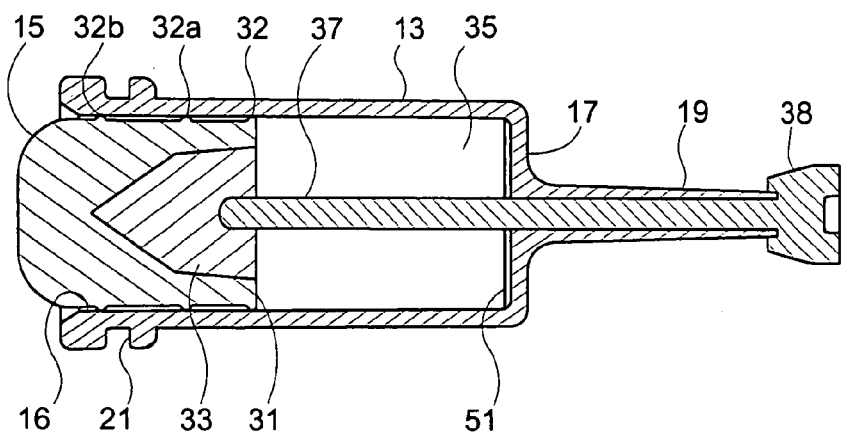
FIG. 2 shows the capsule of FIG. 1 in the activated condition (mixing position)
Figure 3:
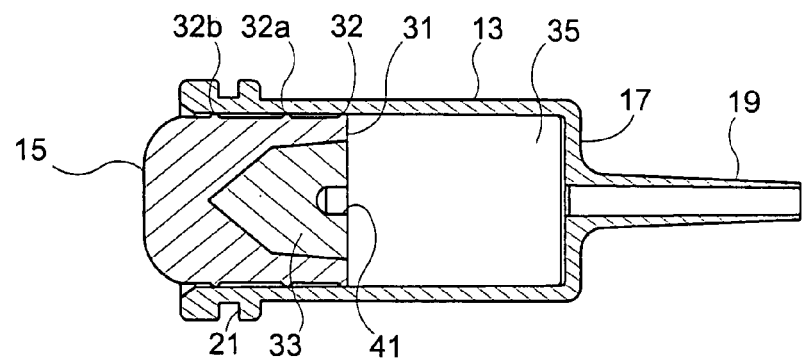
FIG. 3 shows the capsule of FIG. 2 after the activation pin has been withdrawn (discharge position)

FIGS. 1 to 4 show a mixing capsule 11 in accordance with the invention with an outer container part 13 and a piston 15 received in the container part 15. The piston 15 can be axially displaced in the container part 13 and in FIG. 1 is shown in the initial or filled position, while FIG. 2 shows it in the mixing position (activated condition of the capsule). The container part 13 is cylindrical and has an opening 16 for the insertion of the piston is and a front face 17 on which there is formed a discharge nozzle 19. An annular groove 21 is provided on the outside at the rear end of the container part. The annular groove 21 serves to engage with the jaw of a discharge tool well known to persons skilled in the art.

A liquid receptacle 23 is provided on the piston 15. According to the advantageous embodiment here shown, the piston 15 has the shape of a cup with an opening 25 and an internal space 27. The internal space 27 serves to accommodate the liquid component of a two-component resins and serves as a liquid receptacle 23 of stable shape. The opening 25 is closed by a foil or membrane 29 when in the non-activated state. The foil is welded in a known manner onto the front face 31 of the piston 15. One or more annular gaskets 32 are formed on the piston jacket to provide a seal between the piston 15 and the container part 13. The first gasket 32 is situated at the forward edge of the piston. Two further gasket 32a, 32b are situated at some distance from the first gasket 32.

When the mixing capsule is assembled, a mixing chamber 35 is defined between the front face of the piston 15 and the container part 13. An activation part 33 is inserted in the mixing chamber between the front faces of the piston 15 and the container part 13. The activation part 33 is preferably designed as a displacement body having a shape that is complementary to the interior space 27. By means of an activation pin 37 accommodated in the discharge nozzle, the activation part 33 can be axially displaced within the container part 13. The length of the activation pin 37 is at least such as to make it possible for the activation part 33 to be pushed completely into the liquid receptacle. The activation pin 37 has a head 38 that serves as a stop. The head 38 has an undercut 40 in which the front end of the discharge nozzle can become accommodated when the activation pin 37 is pushed fully inwards.

Figure 4:
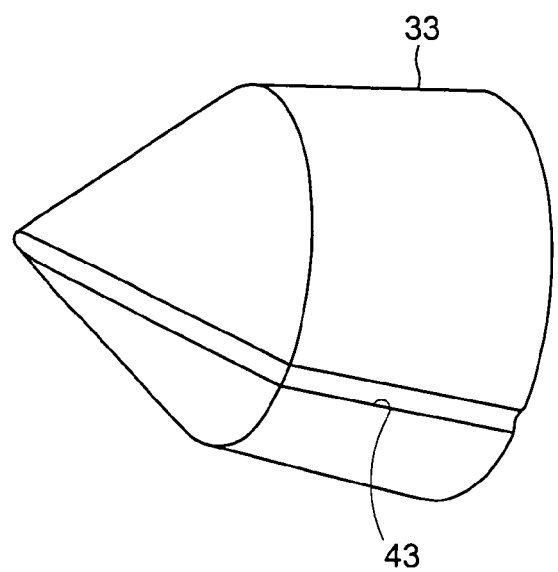
FIG. 4 shows a conical activation part.

The bottom 39 of the activation part 33 is provided with a round recess 41. The recess 41 serves to accommodate the front part of the activation pin 37. Advantageously, the front part of the activation pin 37 and the recess 41 are designed in such a manner as to realize a friction joint. The activation part 33 is thereby fixed in the mixing chamber of the non-activated capsule 11. But one can also think of providing the activation part with radially projecting arms, so that it will be guided inside the container part 13. With a view to assuring that the liquid present in the liquid receptacle can flow into the mixing chamber 35 without hindrance, an overflow channel 43 is provided in the jacket of the activation part (FIG. 4).

Figure 5:
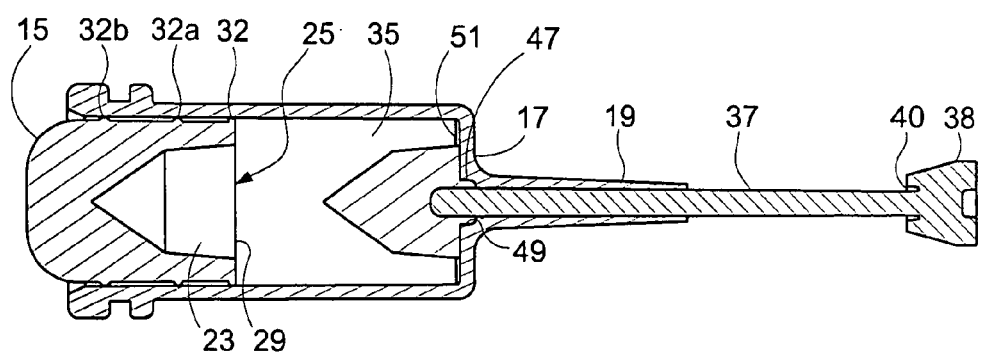
FIG. 5 shows a second embodiment of a mixing capsule with an activation part that can be fixed to the bottom of the container.
Figure 6:
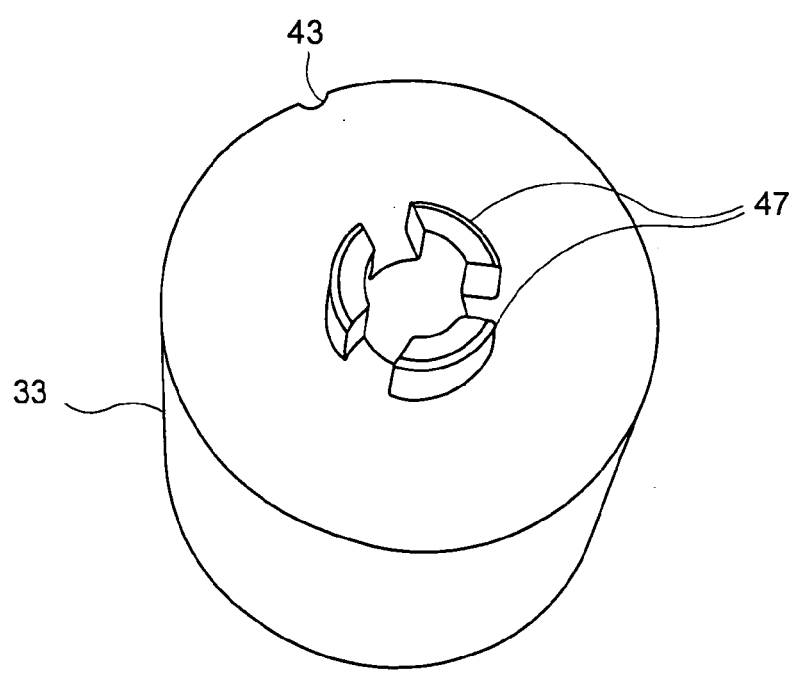
FIG. 6 shows a perspective view of an embodiment of the activation part 33 with annular projections on the bottom.

A modified embodiment of the activation part 33 envisages the provision on the bottom of the activation part of means to fix the activation part 33 in a detachable manner to the container part 13. As shown in FIGS. 5 and 6, these means can be annular projections 47 that can engage with an annular groove 49 in the container bottom 51. The annular groove 49 is provided around the opening of the discharge nozzle 19. The shown embodiment has the advantage that when the capsule is filled, the activation may first be inserted in the container part 13 and that thereafter an undesired drop-out or sliding is prevented by the friction connection between the annular groove 49 and the projections 47.

The mixing capsule in accordance with the invention is prepared and used as follows: The activation and displacement part 33 is first inserted in the container part 13 and the activation pin is then pushed inwards through the discharge nozzle 19 until the front part of the activation pin becomes accommodated in the recess 41. Subsequently, a synthetic resin component (pulverous or liquid) is filled into the vertically oriented container part 13.

The piston 15, which also serves as the liquid receptacle 23, is filled with the desired liquid in a separate operation and then tightly sealed. These processes can be performed in an automated manner. The filling of the piston 15 through the opening 25 and the welding of the foil to the edge of the piston by means of hot punch can be very readily be performed from above.

Thereafter the piston is inserted into the container part 13. With a view to avoiding a pressure build-up in the mixing chamber, a wire may be inserted between the container wall and the piston, so that air can escape from the mixing chamber when the piston is introduced. The wire can then be removed again. The position of the piston 15 in the container part 13 is preferably chosen in such a manner that the piston 15 of the filled mixing capsule can be moved rearwards (outwards) over a certain distance from an initial position (FIG. 1) to a mixing position (FIG. 2). Given the enlarged volume in the mixing position, a low pressure will be created in the mixing chamber. This can be utilized for degassing the mixture during the mixing process. For mixing purposes the capsule is inserted into a known shaking apparatus. This shaking apparatus is provided with two retaining forks arranged at a certain distance from each other and pre-tensioned in opposite directions. The capsule to be mixed is inserted between the forks.

When the capsule 11 is to be activated, the activation body 33 is first pushed into the liquid receptacle 23 with the help of the activation pin 37, after which the entire piston 15 is displaced into the mixing position. When this is done, the spiked displacement body 33 punctures the foil 29 at the centre and presses the liquid synthetic resin component contained in the liquid receptacle into the mixing chamber 35. In the mixing position it then assumes the capsule 11 is shaken in a known shaking apparatus for a certain period of time. The activation pin 37 is then withdrawn and the finished viscous synthetic resin mixture is discharged with a known discharge pistol.

A mixing capsule for a two-component mixture will preferably have a cylindrical container part 13 with a discharge nozzle formed on the front face. A piston is displaceably guided in the container part. An opening is provided on the front face of the piston and leads into a liquid receptacle with a burstable wall or membrane. The membrane closes the opening in the non-activated condition of the capsule. The hollow between the front faces of the container part and the piston constitutes a mixing chamber. A mobile activation part is provided inside the mixing chamber. The activation part can be displaced by means of an activation pin that closes the discharge nozzle in the non-activated condition. In the activated condition of the capsule the activation part is to all intents and purposes completely inserted in the liquid receptacle. The container part 13 and the piston 15 are made of a suitable plastic material.

The mixing capsule in accordance with the invention can be economically produced and filled. It has the advantage that no membrane parts can find their way into the mixing chamber. Furthermore, the entire liquid quantity is always pressed into the mixing chamber, so that a constant quality of the mixings is obtained. Since the capsule is devoid of both threads and undercuts, there is no danger that liquid may be retained in these positions. The edge on the front face of the piston may constitute the filling opening. Given the sufficiently wide contact surface of this edge, foils can be welded onto it a problem-free manner. The piston that serves as liquid receptacle can therefore be filled also with slightly volatile components.

| Legend | |
|---|---|
| 11 | Mixing capsule |
| 13 | Container part |
| 15 | Piston |
| 16 | Opening in the container part 13 for the insertion of the piston 15 |
| 17 | Front face of the container part |
| 19 | Discharge nozzle |
| 21 | Annular groove |
| 23 | Liquid receptacle |
| 25 | Opening (transit opening) |
| 27 | Internal space |
| 29 | Foil or membrane |
| 31 | Front face of piston |
| 32 | Gasket ring or sealing bulge |
| 32a, 32b | Second and third gasket rings |
| 33 | Activation part |
| 35 | Mixing chamber |
| 37 | Activation pin |
| 38 | Head of the activation pin |
| 39 | Bottom of the activation part (= displacement body) |
| 40 | undercut on the head 38 |
| 41 | Recess |
| 43 | Overflow channel |
| 45 | Bottom of the activation part 33 |
| 47 | Projections, for example of annular shape |
| 49 | Annular groove |
| 51 | Bottom of container |

The invention claimed is:

1. A mixing capsule for a two-component mixture comprising:
    a preferably cylindrical container part with an opening and a front face situated opposite it on which front face there is formed a discharge nozzle,
    a piston that can be axially displaced inside the container part, thereby defining a mixture chamber between the front faces of the container part and the piston, the piston having an opening in its front face,
    a receptacle for receiving a liquid being arranged on the piston with a burstable wall or membrane that closes the opening of the piston in the non-activated condition of the capsule,
    wherein the mixture chamber is formed between the front faces of the container part and the piston, and
    a displaceable displacement body having a shape which is complementary to the receptacle so that contents of the liquid receptacle are displaced into the mixing chamber when the displacement body is pushed completely into the receptacle, said displacement body being initially disposed in the mixture chamber between the front faces of the container part and the piston.

2. A mixing capsule in accordance with claim 1, characterized in that the displacement body fits essentially into the opening in the front face of the piston.

3. A mixing capsule in accordance with claim 1, characterized in that in the activated condition of the capsule the displacement body is accommodated in the liquid receptacle substantially flush with the front face of the piston.

4. A mixing capsule in accordance with claim 1, characterized in that the piston constitutes the liquid receptacle.

5. A mixing capsule in accordance with claim 1, characterized in that a membrane covers the opening in the front face of the piston.

6. A mixing capsule in accordance with claim 5, characterized in that the membrane is welded onto the piston.

7. A mixing capsule in accordance with claim 1, characterized in that at least one gasket ring or sealing bulge is formed on an outer surface of the piston.

8. A mixing capsule for a two-component mixture comprising:
- a preferably cylindrical container part with an opening and a front face situated opposite it on which front face there is formed a discharge nozzle,
- a piston that can be axially displaced inside the container part, thereby defining a mixture chamber between the front faces of the container part and the piston, the piston having an opening in its front face,
- a receptacle for receiving a liquid being arranged on the piston with a burstable wall or membrane that closes the opening of the piston in the non-activated condition of the capsule,
- wherein the mixture chamber is formed between the front faces of the container part and the piston, and a displaceable displacement body having a shape which is complementary to the receptacle so that contents of the liquid receptacle are displaced into the mixing chamber when the displacement body is pushed completely into the receptacle, said displacement body being initially disposed in the mixture chamber between the front faces of the container part and the piston,
- and the front part of the displacement body has a tapering tip.

9. A mixing capsule for a two-component mixture comprising:
- a preferably cylindrical container part with an opening and a front face situated opposite it on which front face there is formed a discharge nozzle,
- a piston that can be axially displaced inside the container part, thereby defining a mixture chamber between the front faces of the container part and the piston, the piston having an opening in its front face,
- a receptacle for receiving a liquid being arranged on the piston with a burstable wall or membrane that closes the opening of the piston in the non-activated condition of the capsule,
- wherein the mixture chamber is formed between the front faces of the container part and the piston, and
- a displaceable displacement body having a shape which is complementary to the receptacle so that contents of the liquid receptacle are displaced into the mixing chamber when the displacement body is pushed completely into the receptacle, said displacement body being initially disposed in the mixture chamber between the front faces of the container cart and the piston,
- and an overflow channel extending in the axial direction is provided on an outer surface of the displacement body.

10. A mixing capsule in accordance with claim 1, characterized in that the displacement body can be displaced by an activation pin that closes the discharge nozzle in the non-activated condition.

11. A mixing capsule in accordance with claim 10, characterized in that the displacement body is integral with the activation pin.

12. A mixing capsule in accordance with claim 10, characterized in that a predetermined breaking point is provided between the displacement body and the activation pin.

13. A mixing capsule in accordance with claim 10, characterized in that a recess that serves as a guide for the activation pin is provided on the bottom of the displacement body.

14. A mixing capsule in accordance with claim 1, characterized in that the displacement body is a filling body with a flat bottom.

15. A method of activating a mixing capsule for receiving at least two components of a multi-component mixture said mixing capsule having a mixing chamber defined by a cylindrical containing part with an opening at one end and a front face at the other end on which there is formed a discharge nozzle, and a piston that can be axially displaced inside the containing part, the piston having an opening in its front face, a receptacle for receiving a liquid being arranged in or on the piston with a burstable wall or membrane that closes the opening of the piston in the non-activated condition of the capsule, in which method a membrane or foil that separates the mixing chamber containing a pulverous component from the liquid receptacle is destroyed and the content of the liquid receptacle is pressed into the mixing chamber, characterized in that the membrane is destroyed by pushing a displaceable displacement body having a shape which is complementary to the liquid receptacle into the liquid receptacle, said displacement body being initially disposed in the mixing chamber between the front face of said mixing capsule and said piston.

16. Method of activating a mixing capsule for receiving at least two components of a multi-component mixture said mixing capsule having a mixing chamber defined by a cylindrical containing part with an opening at one end and a front face at the other end, on which there is formed a discharge nozzle, and a piston that can be axially displaced inside the containing part, the piston having an opening in its front face, a liquid receptacle arranged in or on the piston with a burstable wall or membrane that closes the opening of the piston in the non-activated condition of the capsule, in which method a membrane or foil that separates the mixing chamber containing a pulverous component from the liquid receptacle is destroyed and the content of the liquid receptacle is pressed into the mixing chamber, characterized in that the membrane is destroyed by pushing a displaceable activation part into the liquid receptacle, said displacement body being initially disposed in the mixing chamber between the front face of said mixing capsule and said piston.

17. A method in accordance with claim 16, characterized in that the activation part presses the liquid from the liquid receptacle into the mixing chamber.

18. A method in accordance with claim 16, characterized in that mixing chamber is enlarged before the mixing, so that the mixing process takes place in low-pressure conditions.

19. A method in accordance with claim 15, characterized in that mixing chamber is enlarged before the mixing, so that the mixing process takes place in low-pressure conditions.

20. The mixing capsule claimed in claim 1, wherein the displacement body has a tapering tip.

21. The mixing capsule claimed in claim 9, wherein the displacement body has a tapering tip.

22. The mixing capsule claimed in claim 15, wherein the displacement body has a tapering tip.

23. The mixing capsule claimed in claim 16, wherein the displacement body has a tapering tip.

* * * * *